United States Patent
Kumada (10) Patent No.: US 10,881,400 B2
(45) Date of Patent: Jan. 5, 2021

(54) MEDICAL STAPLER SYSTEM

(71) Applicant: OLYMPUS CORPORATION, Tokyo (JP)

(72) Inventor: Yoshiyuki Kumada, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 191 days.

(21) Appl. No.: 16/299,439

(22) Filed: Mar. 12, 2019

(65) Prior Publication Data
US 2019/0200982 A1    Jul. 4, 2019

Related U.S. Application Data

(63) Continuation of application No. PCT/JP2016/084293, filed on Nov. 18, 2016.

(51) Int. Cl.
*A61B 17/064*    (2006.01)
*A61B 17/072*    (2006.01)
(Continued)

(52) U.S. Cl.
CPC .......... *A61B 17/072* (2013.01); *A61B 17/064* (2013.01); *A61B 17/0644* (2013.01);
(Continued)

(58) Field of Classification Search
CPC . A61B 17/064; A61B 17/0644; A61B 17/068; A61B 17/0686; A61B 17/072;
(Continued)

(56) References Cited

U.S. PATENT DOCUMENTS 4,434,796 A    3/1984   Karapetian et al.
5,147,381 A    9/1992   Heimerl et al.
(Continued)

FOREIGN PATENT DOCUMENTS

EP    0 497 412 A1    8/1992
EP    1769755 A2     4/2007
(Continued)

OTHER PUBLICATIONS

Japanese Office Action dated Apr. 21, 2020 in Japanese Patent Application No. 2018-518017.
(Continued)

*Primary Examiner* — Scott A Smith
(74) *Attorney, Agent, or Firm* — Scully, Scott, Murphy & Presser, P.C.

(57) ABSTRACT

A medical stapler system according to the present invention is equipped with a medical stapler and a staple that closes tissue. The medical stapler is equipped with: a first grasper and a second grasper that have a longitudinal axis and that grasp the tissue therebetween when in a closed state; a holder that retains the staple; a housing body that houses the holder while a needle of the staple projects from a first contact surface of the first grasper; and a drive mechanism that slides the holder along the longitudinal axis. The second grasper has a second contact surface that grasps the tissue between the first contact surface and the second contact surface, a recessed portion that houses the needle without causing penetration or deformation when a closed state, and an anvil against which the needle is pushed and deformed when the closed state.

4 Claims, 10 Drawing Sheets

(51) Int. Cl.
  *A61B 17/29* (2006.01)
  *A61B 17/10* (2006.01)
  *A61B 17/068* (2006.01)
  *A61B 17/115* (2006.01)

(52) U.S. Cl.
  CPC .......... *A61B 17/0684* (2013.01); *A61B 17/10* (2013.01); *A61B 17/29* (2013.01); *A61B 17/115* (2013.01); *A61B 2017/07214* (2013.01); *A61B 2017/07221* (2013.01); *A61B 2017/07228* (2013.01); *A61B 2017/07257* (2013.01); *A61B 2017/07264* (2013.01); *A61B 2017/07271* (2013.01); *A61B 2017/07278* (2013.01); *A61B 2017/2936* (2013.01)

(58) Field of Classification Search
  CPC ........ A61B 17/07207; A61B 17/07292; A61B 17/115; A61B 2017/07214; A61B 2017/07264; A61B 2017/07271; A61B 2017/07278; A61B 2017/07228
  USPC .............. 227/19, 175.1, 176.1, 189.1, 180.1; 606/1, 139, 143, 151, 153, 219, 223
  See application file for complete search history.

(56) References Cited

U.S. PATENT DOCUMENTS

| | | | |
|---|---|---|---|
| 5,208,661 A | 5/1993 | Jaspers | |
| 5,342,396 A | 8/1994 | Cook | |
| 5,456,400 A * | 10/1995 | Shichman | A61B 17/064 227/176.1 |
| 5,591,178 A | 1/1997 | Green et al. | |
| 5,720,756 A | 2/1998 | Green et al. | |
| 5,725,537 A | 3/1998 | Green et al. | |
| 5,725,538 A | 3/1998 | Green et al. | |
| 5,779,718 A | 7/1998 | Green et al. | |
| 5,843,084 A * | 12/1998 | Hart | A61B 17/064 606/77 |
| 5,868,761 A | 2/1999 | Nicholas et al. | |
| 6,099,537 A | 8/2000 | Sugai et al. | |
| 6,306,149 B1 * | 10/2001 | Meade | A61B 17/1285 606/143 |
| 6,994,714 B2 * | 2/2006 | Vargas | A61B 17/064 227/175.1 |
| 7,918,376 B1 * | 4/2011 | Knodel | A61B 17/07207 227/175.1 |
| 8,056,789 B1 | 11/2011 | White et al. | |
| 8,157,145 B2 | 4/2012 | Shelton, IV et al. | |
| 8,225,980 B1 | 7/2012 | Rivera | |
| 8,365,973 B1 | 2/2013 | White et al. | |
| 8,439,246 B1 | 5/2013 | Knodel | |
| 8,662,369 B1 | 3/2014 | Manoux et al. | |
| 8,978,954 B2 | 3/2015 | Shelton, IV et al. | |
| 9,788,835 B2 * | 10/2017 | Morgan | A61B 17/0644 |
| 9,877,722 B2 * | 1/2018 | Schellin | A61B 17/064 |
| 9,907,554 B2 * | 3/2018 | Morgan | A61B 17/07207 |
| 10,004,496 B2 * | 6/2018 | Shelton, IV | A61B 17/0644 |
| 2003/0120308 A1 | 6/2003 | Loubens et al. | |
| 2004/0006372 A1 | 1/2004 | Racenet et al. | |
| 2004/0046001 A1 | 3/2004 | Jairam | |
| 2004/0094597 A1 | 5/2004 | Whitman et al. | |
| 2004/0267310 A1 | 12/2004 | Racenet et al. | |
| 2005/0203547 A1 | 9/2005 | Weller et al. | |
| 2005/0203548 A1 | 9/2005 | Weller et al. | |
| 2006/0124688 A1 | 6/2006 | Racenet et al. | |
| 2006/0151568 A1 | 7/2006 | Weller et al. | |
| 2006/0253143 A1 * | 11/2006 | Edoga | A61B 17/10 606/153 |
| 2006/0278679 A1 | 12/2006 | Viola et al. | |
| 2007/0057014 A1 | 3/2007 | Whitman et al. | |
| 2007/0068990 A1 | 3/2007 | Shelton, IV et al. | |
| 2007/0075114 A1 | 4/2007 | Shelton, IV et al. | |
| 2007/0106329 A1 | 5/2007 | Dabir et al. | |
| 2007/0167960 A1 | 7/2007 | Roth et al. | |
| 2007/0233161 A1 | 10/2007 | Weller et al. | |
| 2007/0295780 A1 | 12/2007 | Shelton et al. | |
| 2008/0061109 A1 | 3/2008 | Racenet et al. | |
| 2008/0078800 A1 | 4/2008 | Hess et al. | |
| 2008/0078807 A1 | 4/2008 | Hess et al. | |
| 2009/0065552 A1 * | 3/2009 | Knodel | A61B 17/115 227/180.1 |
| 2010/0006620 A1 | 1/2010 | Sorrentino et al. | |
| 2010/0023054 A1 | 1/2010 | Matsutani et al. | |
| 2010/0133321 A1 | 6/2010 | Racenet et al. | |
| 2010/0187283 A1 | 7/2010 | Crainich et al. | |
| 2010/0191255 A1 | 7/2010 | Crainich et al. | |
| 2010/0191262 A1 | 7/2010 | Harris et al. | |
| 2010/0191282 A1 | 7/2010 | Harris et al. | |
| 2010/0198256 A1 | 8/2010 | Loubens et al. | |
| 2010/0301093 A1 | 12/2010 | Viola | |
| 2011/0017799 A1 | 1/2011 | Whitman et al. | |
| 2011/0068145 A1 | 3/2011 | Bedi et al. | |
| 2011/0108603 A1 | 5/2011 | Racenet et al. | |
| 2011/0168756 A1 | 7/2011 | Racenet et al. | |
| 2012/0061448 A1 | 3/2012 | Zingman | |
| 2012/0080497 A1 | 4/2012 | White et al. | |
| 2012/0125971 A1 | 5/2012 | Holcomb et al. | |
| 2012/0145768 A1 | 6/2012 | Sorrentino et al. | |
| 2012/0160890 A1 | 6/2012 | Holcomb et al. | |
| 2012/0160891 A1 | 6/2012 | Harris et al. | |
| 2012/0193390 A1 | 8/2012 | Racenet et al. | |
| 2012/0223121 A1 | 9/2012 | Viola et al. | |
| 2012/0234897 A1 | 9/2012 | Shelton, IV et al. | |
| 2012/0241501 A1 | 9/2012 | Swayze et al. | |
| 2012/0318844 A1 | 12/2012 | Shelton, IV et al. | |
| 2013/0048697 A1 | 2/2013 | Shelton, IV et al. | |
| 2013/0075448 A1 | 3/2013 | Schmid et al. | |
| 2013/0105551 A1 | 5/2013 | Zingman | |
| 2013/0126585 A1 | 5/2013 | White et al. | |
| 2013/0172929 A1 | 7/2013 | Hess et al. | |
| 2013/0233905 A1 | 9/2013 | Sorrentino et al. | |
| 2014/0103091 A1 | 4/2014 | Whitman et al. | |
| 2014/0151435 A1 | 6/2014 | Holcomb et al. | |
| 2014/0175153 A1 | 6/2014 | Manoux et al. | |
| 2014/0183243 A1 | 7/2014 | Racenet et al. | |
| 2014/0326777 A1 | 11/2014 | Zingman | |
| 2014/0332580 A1 | 11/2014 | White et al. | |
| 2015/0173748 A1 | 6/2015 | Marczyk et al. | |
| 2015/0173756 A1 | 6/2015 | Baxter, III et al. | |
| 2015/0342606 A1 | 12/2015 | Schmid et al. | |
| 2015/0374363 A1 | 12/2015 | Laurent, IV et al. | |
| 2016/0058441 A1 * | 3/2016 | Morgan | A61B 17/07207 606/219 |
| 2016/0113653 A1 | 4/2016 | Zingman | |
| 2016/0174983 A1 | 6/2016 | Shelton, IV et al. | |
| 2016/0183945 A1 | 6/2016 | Shelton, IV et al. | |
| 2016/0199061 A1 | 7/2016 | Shelton, IV et al. | |
| 2016/0199089 A1 | 7/2016 | Hess et al. | |
| 2017/0143338 A1 | 5/2017 | Sorrentino et al. | |
| 2017/0281159 A1 | 10/2017 | Holcomb et al. | |
| 2017/0296175 A1 | 10/2017 | Kumada et al. | |
| 2019/0059894 A1 | 2/2019 | Kumada et al. | |

FOREIGN PATENT DOCUMENTS

| | | | |
|---|---|---|---|
| EP | 1785100 | A1 | 5/2007 |
| EP | 1862129 | A2 | 12/2007 |
| EP | 1872727 | A1 | 1/2008 |
| EP | 2380502 | A1 | 10/2011 |
| EP | 2380503 | A1 | 10/2011 |
| EP | 2382926 | A1 | 11/2011 |
| EP | 2382927 | A1 | 11/2011 |
| EP | 2 944 271 | A1 | 11/2015 |
| GB | 2098694 | A | 11/1982 |
| JP | S48-65091 | U1 | 8/1973 |
| JP | S57-177739 | A | 11/1982 |
| JP | H04-227245 | A | 8/1992 |
| JP | H05-068260 | A | 3/1993 |
| JP | H07-124166 | A | 5/1995 |
| JP | H07-236644 | A | 9/1995 |
| JP | H08-507708 | A | 8/1996 |
| JP | H09-224944 | A | 9/1997 |

(56) References Cited

FOREIGN PATENT DOCUMENTS

| | | |
|---|---|---|
| JP | 2001-017436 A | 1/2001 |
| JP | 2002-320620 A | 11/2002 |
| JP | 2003-534031 A | 11/2003 |
| JP | 2004-097714 A | 4/2004 |
| JP | 2005-160933 A | 6/2005 |
| JP | 2006-334413 A | 12/2006 |
| JP | 2007-117725 A | 5/2007 |
| JP | 2007-130457 A | 5/2007 |
| JP | 2008-029831 A | 2/2008 |
| JP | 2008-93480 A | 4/2008 |
| JP | 4101650 B2 | 6/2008 |
| JP | 2010-504846 A | 2/2010 |
| JP | 2010-514505 A | 5/2010 |
| JP | 2011-56277 A | 3/2011 |
| JP | 2012-515631 A | 7/2012 |
| JP | 5198454 B2 | 5/2013 |
| JP | 2013-534159 A | 9/2013 |
| JP | 2013-537066 A | 9/2013 |
| JP | 5329956 B2 | 10/2013 |
| JP | 2014-144365 A | 8/2014 |
| JP | 2014-531264 A | 11/2014 |
| JP | 2015-513958 A | 5/2015 |
| WO | WO 1994/020030 A1 | 9/1994 |
| WO | WO 2002/032322 A2 | 4/2002 |
| WO | WO 2004/024395 A2 | 3/2004 |
| WO | WO 2005/092210 A1 | 10/2005 |
| WO | WO 2007/014354 A2 | 2/2007 |
| WO | WO 2007/078988 A2 | 7/2007 |
| WO | WO 2008/042044 A2 | 4/2008 |
| WO | WO 2008/082844 A2 | 7/2008 |
| WO | WO 2008/084722 A1 | 7/2008 |
| WO | WO 2009/038550 A1 | 3/2009 |
| WO | 2010/085725 A1 | 7/2010 |
| WO | WO 2012/021671 A1 | 2/2012 |
| WO | WO 2012/033960 A2 | 3/2012 |
| WO | WO 2013/148779 A2 | 10/2013 |
| WO | WO 2016/014072 A1 | 1/2016 |
| WO | WO 2016/075740 A1 | 5/2016 |
| WO | WO 2017/122319 A1 | 7/2017 |
| WO | WO 2017/126128 A1 | 7/2017 |
| WO | WO 2017/199392 A1 | 11/2017 |
| WO | WO 2017/199411 A1 | 11/2017 |

OTHER PUBLICATIONS

Office Action dated May 14, 2020 received in U.S. Appl. No. 16/170,139.
Japanese Office Action dated Nov. 19, 2019 in Japanese Patent Application No. 2017-561461.
Japanese Office Action dated Feb. 12, 2020 in Japanese Patent Application No. 2017-561461.
International Search Report dated Feb. 7, 2017 issued in PCT/JP2016/084293.
International Search Report dated Jan. 20, 2015 issued in PCT/JP2014/079732.
International Search Report dated Aug. 23, 2016 issued in PCT/JP2016/064964.
International Search Report dated Feb. 9, 2016 issued in PCT/JP2016/050960.
International Search Report dated Aug. 23, 2016 issued in PCT/JP2016/064861.

* cited by examiner

MEDICAL STAPLER SYSTEM

CROSS-REFERENCE TO RELATED APPLICATIONS

This is a continuation of International Application PCT/JP2016/084293, with an international filing date of Nov. 18, 2016, which is hereby incorporated by reference herein in its entirety.

TECHNICAL FIELD

The present invention relates to a medical stapler system.

BACKGROUND ART

A medical stapler that grasps tissue between a pair of jaws and pushes out a staple from one of the jaws while deforming the staple with the other jaw is known (for example, see Japanese Patent No. 5198454).

A medical stapler in which a cartridge containing lined-up staples is loaded inside a pair of jaws that grasp the tissue and a staple is deformed by closing the jaws is also known (for example, see Japanese Translation of PCT International Application, Publication No. 2014-531264).

SUMMARY OF INVENTION

According to an aspect of the present invention, there is provided a medical stapler system including a medical stapler and a staple that is configured to be deformed by the medical stapler to close tissue. The medical stapler includes: a first grasper and a second grasper that are pivotably connected to each other so as to open and close relative to each other and that have a longitudinal axis so that the tissue is grasped between the first and second graspers when in a closed state; a holder that retains the staple; a housing body that houses the holder while needles of the staple project from a first contact surface of the first grasper to be closely attached to the tissue when in the closed state; and a drive mechanism that is configured to slide the holder in the housing body along the longitudinal axis. The second grasper has a second contact surface that grasps the tissue between the first contact surface and the second contact surface when in the closed state. The second contact surface has a recessed portion that houses the needles without causing penetration or deformation when the closed state is created and the holder is positioned on one side in the longitudinal axis direction, and an anvil against which the needles are pushed and deformed when the closed state is created and the holder is positioned on the other side in the longitudinal axis direction.

DESCRIPTION OF EMBODIMENTS

A medical stapler system 1 according to one embodiment of the present invention will now be described with reference to the drawings.

Figure 1:
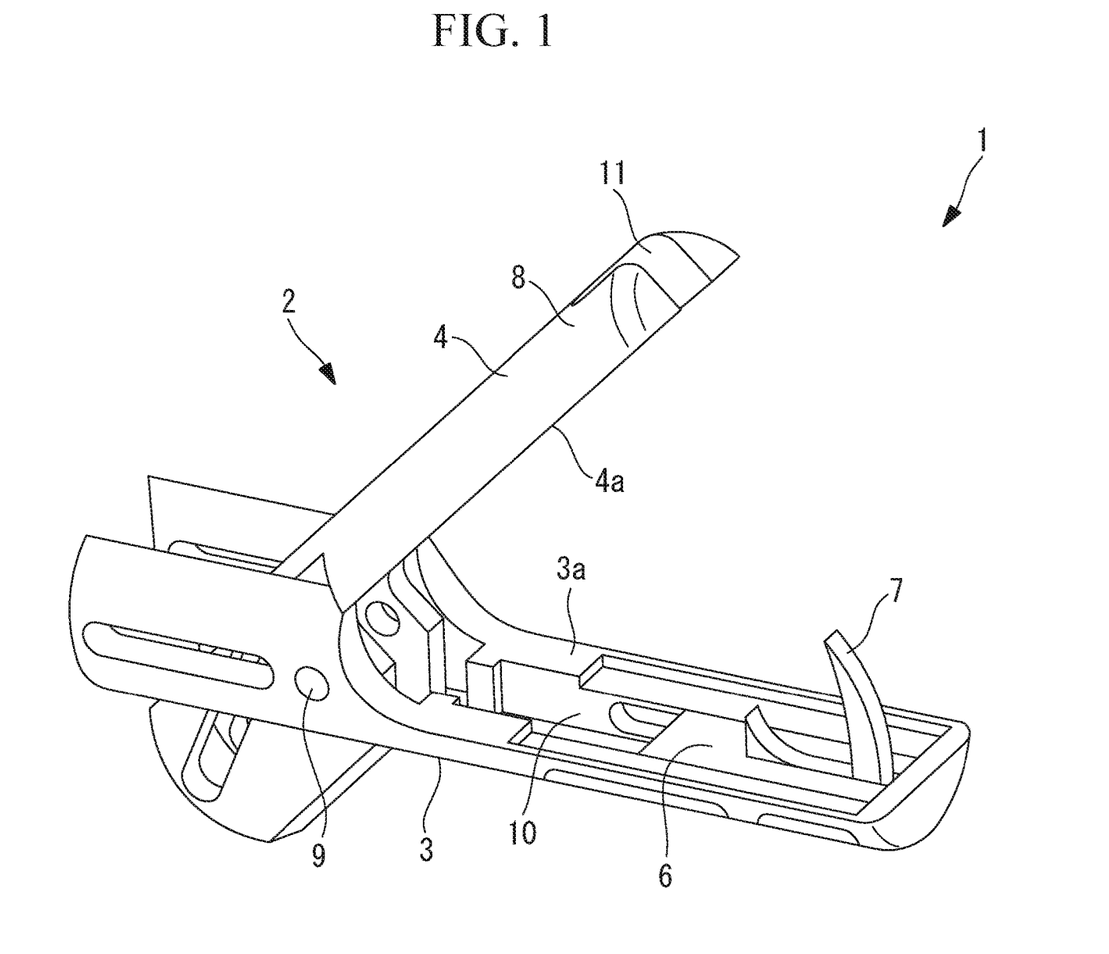
FIG. 1 is a diagram illustrating the overall structure of a medical stapler system according to one embodiment of the present invention.

As illustrated in FIG. 1, the medical stapler system 1 of this embodiment includes a medical stapler 2 and a staple 7 to be deformed by the medical stapler 2 to close tissue.

Figure 2:
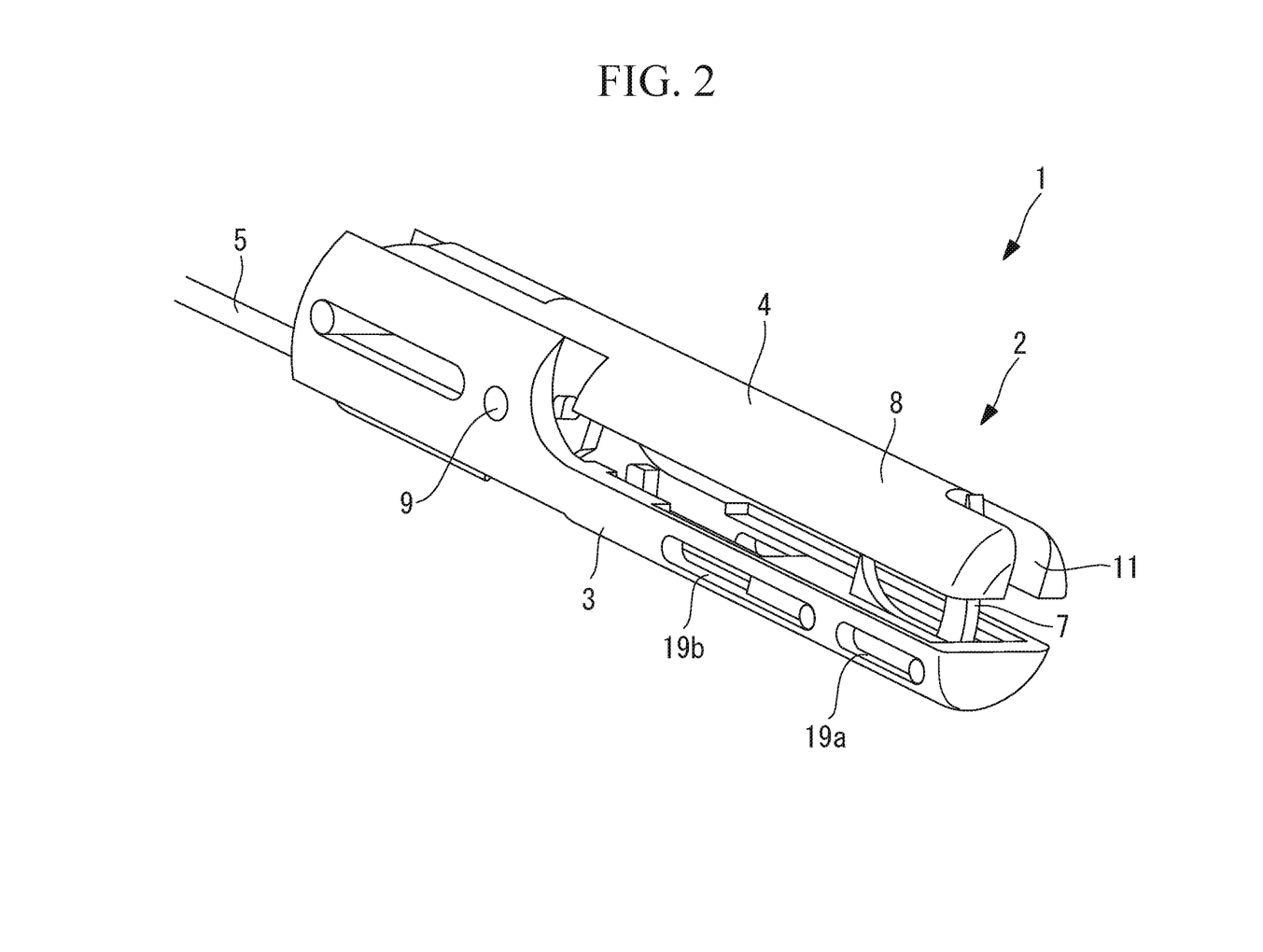
FIG. 2 is a diagram illustrating the medical stapler system illustrated in FIG. 1 in a closed state.

As illustrated in FIGS. 1 and 2, the medical stapler 2 includes: straight bar-shaped first and second graspers 3 and 4 that can be opened and closed relative to each other on a pivot axis and that grasp tissue A therebetween when in a closed state; a holder 6 housing the staple 7; and a drive mechanism 5 that slides the holder 6 along a longitudinal axis of the first grasper 3. The first grasper 3 is equipped with a first contact surface 3a that closely attaches to one side of the tissue A when in a closed state, and a housing body 10 that houses the holder 6 that retains the staple 7.

Figure 3A:
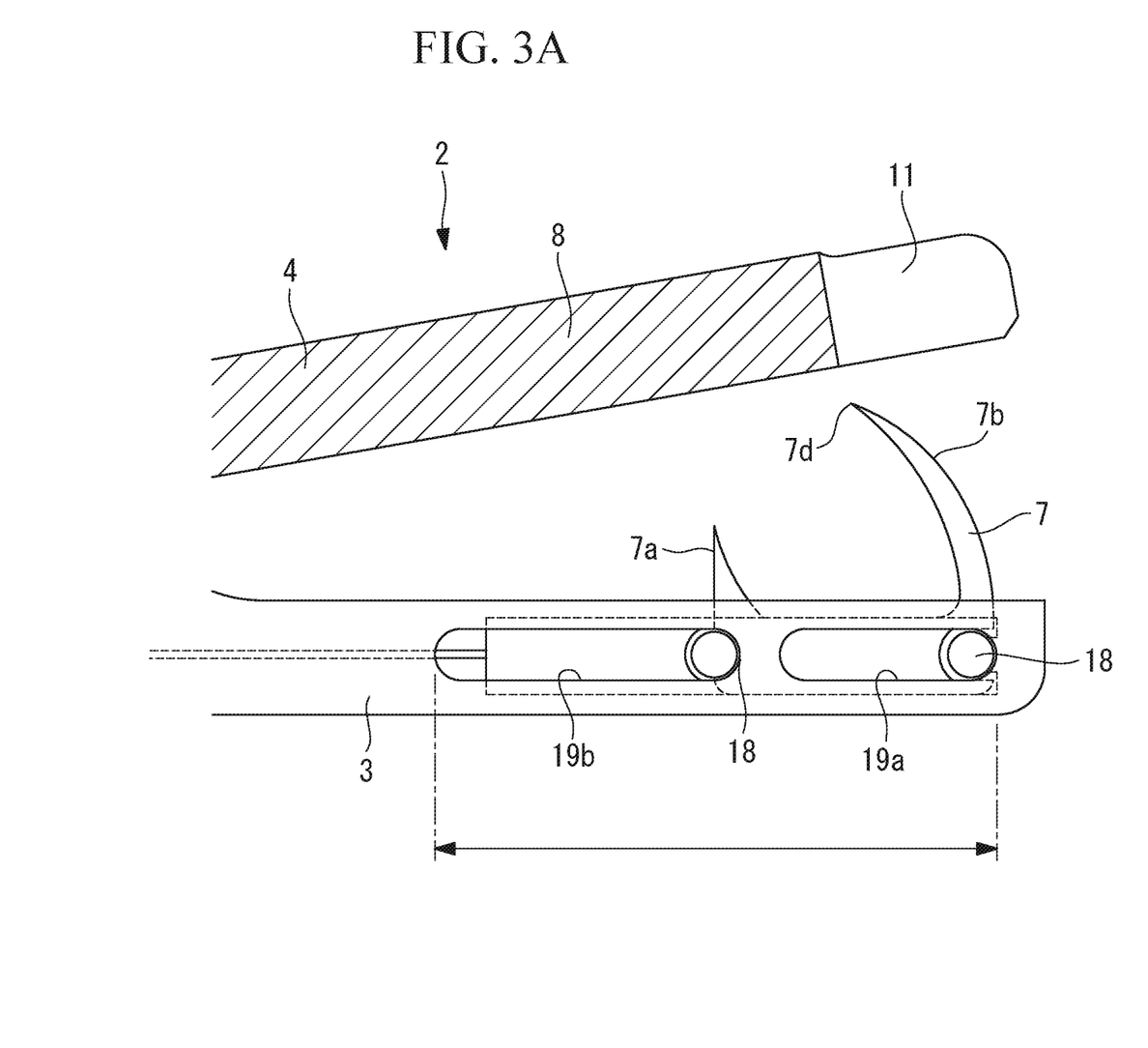
FIG. 3A is a vertical sectional view illustrating a distal end portion of the medical stapler system illustrated in FIG. 1.

The housing body 10 is a recessed portion that opens toward the first contact surface 3a, and when the holder 6 retaining the staple 7 is housed in the housing body 10, needles 7a and 7b of the staple 7 are arranged to protrude from the first contact surface 3a with pointed ends thereof directed toward the second grasper 4 (see FIG. 3A).

The second grasper 4 is equipped with a second contact surface 4a that closely attaches to the other side of the tissue A when in a closed state, a recessed portion 11 that receives the needles of the staple 7, and an anvil 8 against which the needle 7b is pressed and deformed.

Figure 3B:
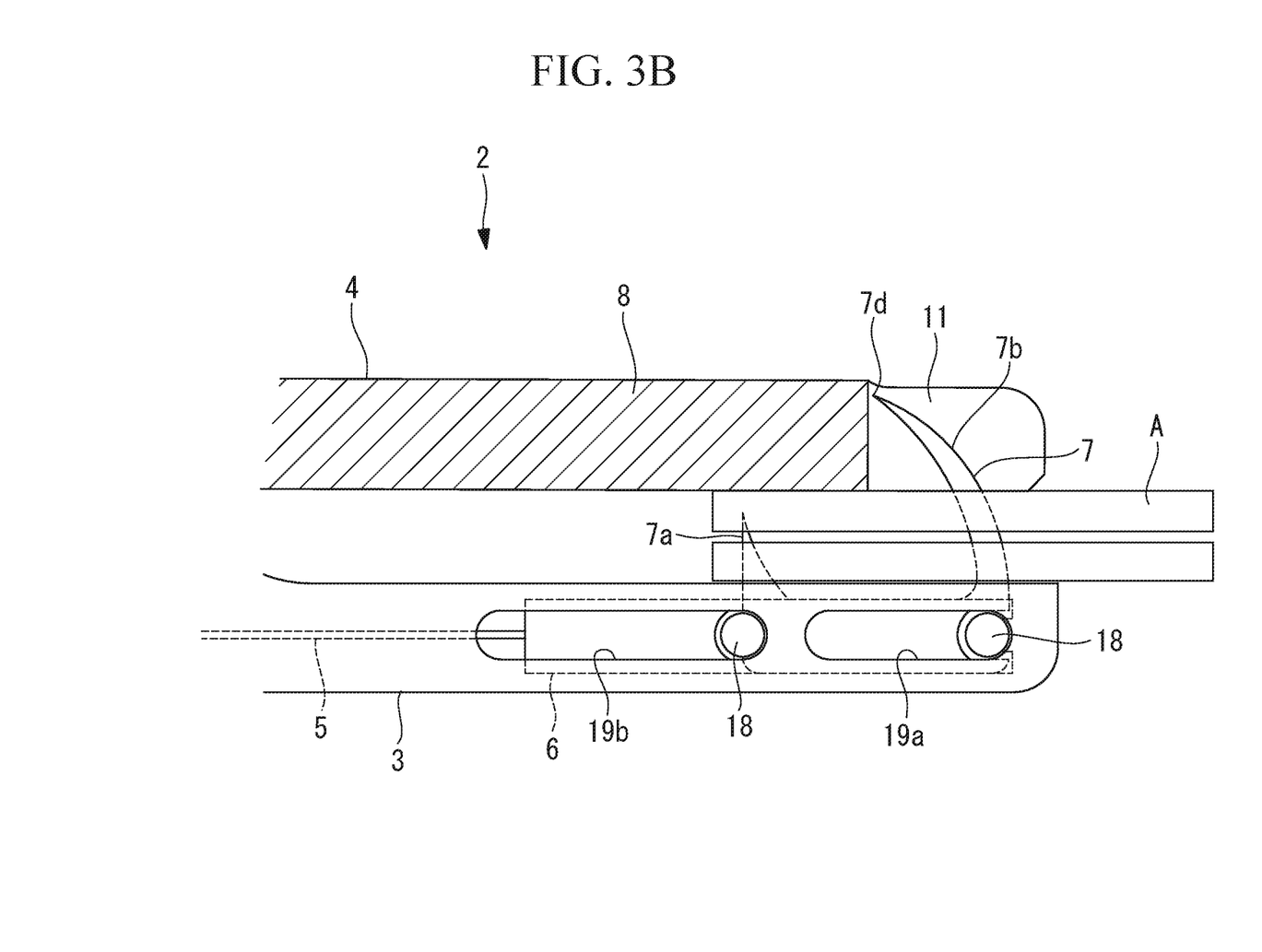
FIG. 3B is a vertical sectional view illustrating the distal end portion of the medical stapler system illustrated in FIG. 3A in a closed state.

As illustrated in FIG. 3B, the second grasper 4 has a thickness such that the needles 7a and 7b of the staple 7 protruding from the first contact surface 3a do not penetrate therein. In addition, the recessed portion 11 is sized so that even in a closed state, the staple 7 is housed without having the needles 7a and 7b contacting the recessed portion 11.

Figure 3C:
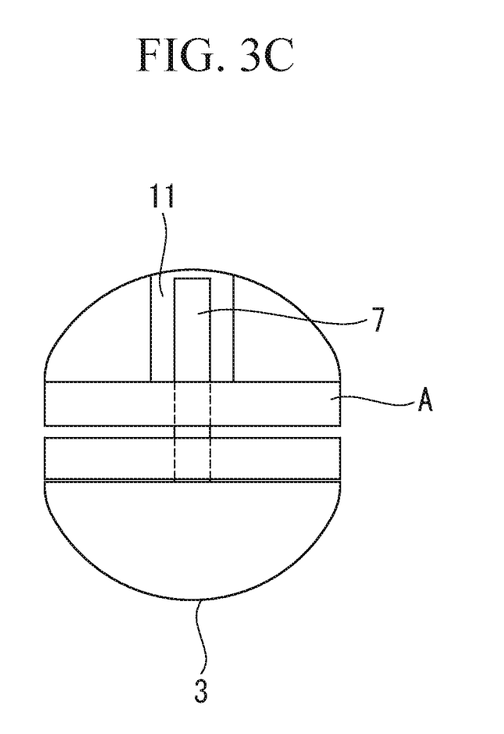
FIG. 3C is a front view illustrating the distal end portion of the medical stapler system illustrated in FIG. 3B.

As illustrated in FIG. 3C, when in a closed state, the first contact surface 3a of the first grasper 3 and the second contact surface 4a of the second grasper 4, which is present on both the right and left sides of the recessed portion 11, are parallel to and face each other so that the tissue A is grasped therebetween.

By causing the second grasper 4 to pivot on the pivot axis with respect to the first grasper 3 by using a pivot mechanism 9, the first grasper 3 and the second grasper 4 move relative to each other between an open state illustrated in FIG. 1 in which the members are separated from each other and a closed state illustrated in FIG. 2 in which the members come together to grasp the tissue A therebetween.

Figure 5A:
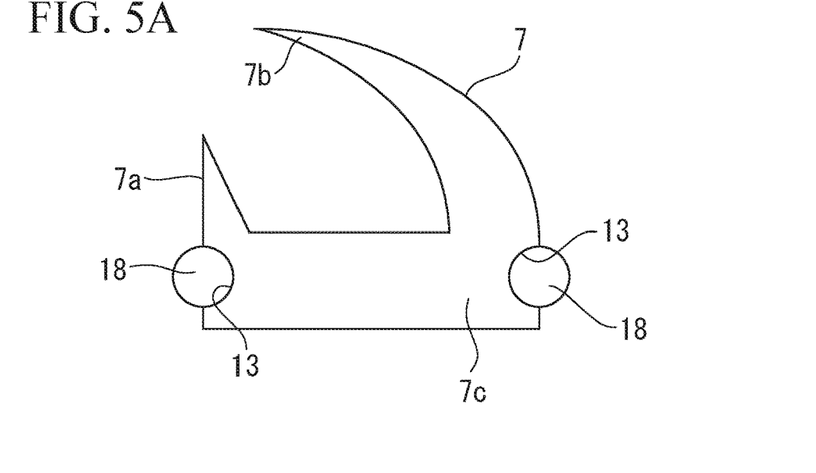
FIG. 5A is a vertical sectional view illustrating one example of the staple used in the medical stapler system illustrated in FIG. 1.

For example, as illustrated in FIG. 5A, the staple 7 has an asymmetric shape constituted by an elongated base portion 7c, a first needle 7a that extends from one end of the base portion 7c in a direction orthogonal to the lengthways direction of the base portion 7c, and a second needle 7b that extends from the other end of the base portion 7c in the direction orthogonal to the lengthways direction of the base portion 7c. The second needle 7b has a needle tip 7d having a curved shape smoothly bending toward the first needle 7a. The first needle 7a and the needle tip 7d of the second needle 7b have sharp, pointed ends that can easily cut into the tissue A. As illustrated in FIG. 5A, pin receiving portions 13 that detachably receive fixing pins 18 described below are disposed on two sides of the base portion 7c.

As illustrated in FIGS. 1 and 2, the staple 7 inside the holder 6 is arranged so that the base portion 7c of the staple 7 extends in a direction along the longitudinal axis of the first grasper 3.

As illustrated in FIGS. 6A to 6D, the staple 7 is designed to close the tissue A by causing the first needle 7a and the second needle 7b to penetrate through the tissue A and then deforming the second needle 7b.

As illustrated in FIGS. 1 to 3B, a pair of first slits 19a that have a straight line shape, extend in the longitudinal axis direction, and penetrate through the housing body, and a pair of second slits 19b that are disposed on the proximal end side of the first slits 19a, are longer than the longitudinal axis of the first slits 19a, and penetrate through the housing body are formed in both side surfaces of the first grasper 3. As illustrated in FIGS. 3A and 3B, a fixing pin 18 is inserted into each of the pair of first slits 19a and the pair of second slits 19b in a direction intersecting the longitudinal axis of the first grasper 3.

Figure 4A:
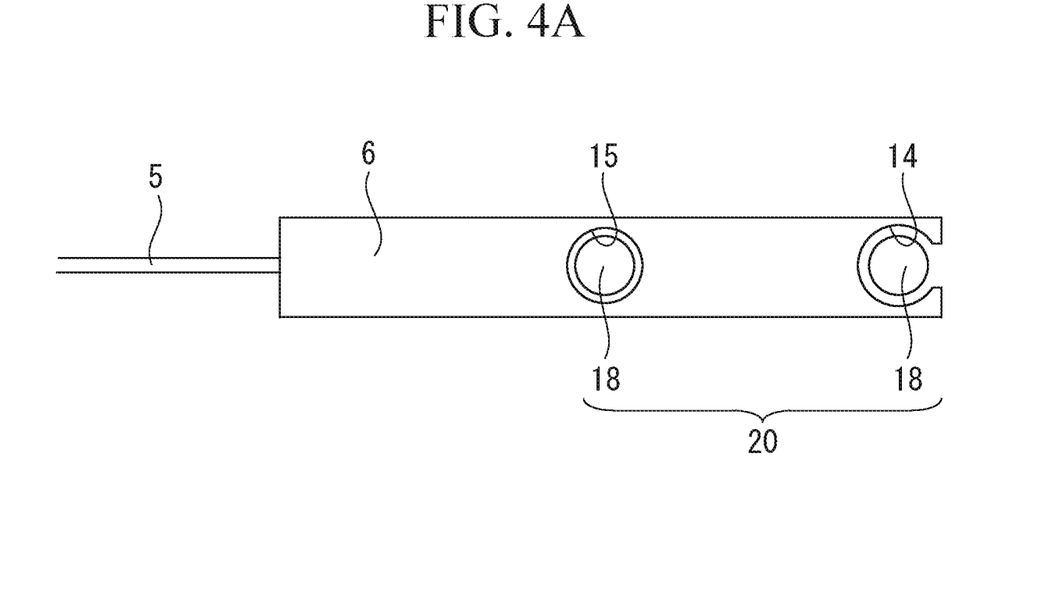
FIG. 4A is a vertical sectional view illustrating a holder used in the medical stapler system illustrated in FIG. 3A.
Figure 4B:
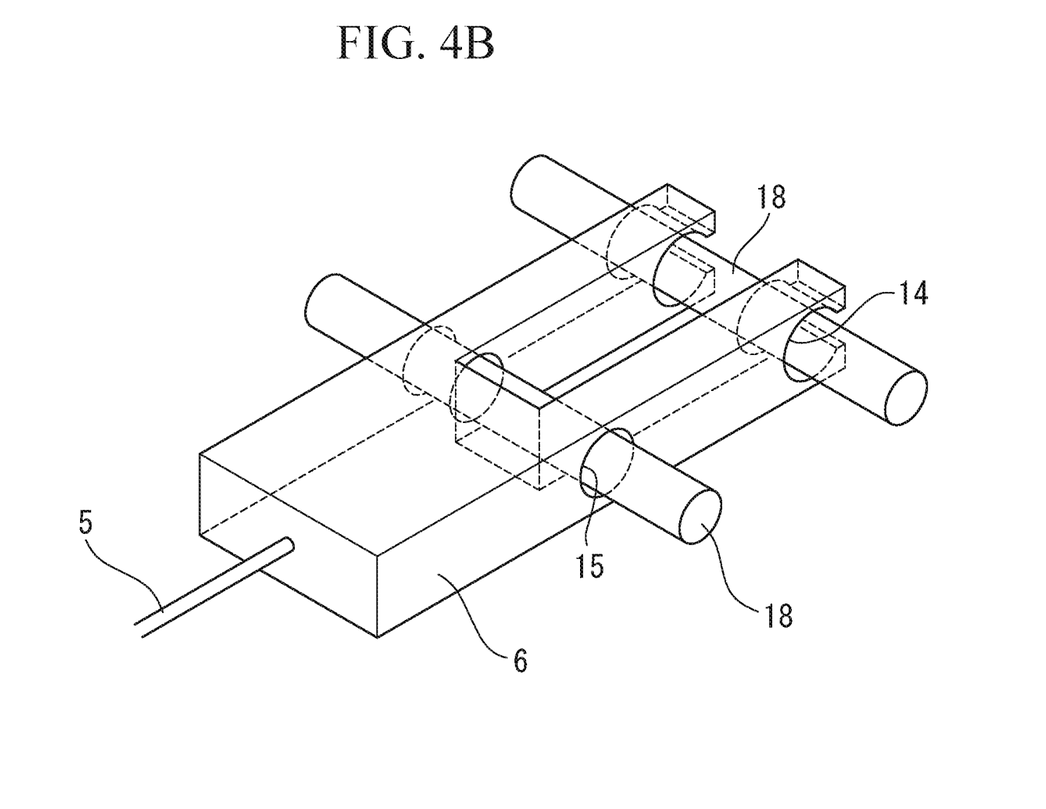
FIG. 4B is a perspective view illustrating a state in which fixing pins are inserted into the holder illustrated in FIG. 4A.

As illustrated in FIG. 4B, the holder 6 has a groove for retaining the base portion 7c of the staple 7, and is equipped with an attach-release mechanism 20 that switches between a state in which the staple 7 is retained in the groove and a state in which the staple 7 is released.

As illustrated in FIGS. 4A and 4B, the attach-release mechanism 20 includes: a pin hole 15 and a fitting recessed portion 14 that hold two fixing pins 18 in the groove in the holder 6 so that the fixing pins 18 are spaced from each other in the longitudinal axis direction and parallel to each other; a fixing pin 18 housed in the pin hole 15 and having two ends housed in the second slits 19b; and a fixing pin 18 fitted to the fitting recessed portion 14 and having two ends housed in the first slits 19a. The staple 7 is released from the holder 6 by detaching the fixing pin 18 from the fitting recessed portion 14.

The holder 6 with the staple 7 fitted into is housed in the housing body 10 of the first grasper 3, and, as illustrated in FIGS. 3A and 3B, the fixing pins 18 are inserted into the first slits 19a and the second slits 19b in the first grasper 3 so as to pass through the fitting recessed portion 14 and the pin hole 15 in the holder 6. As a result, the holder 6 is attached to the first grasper 3 with the fixing pins 18 so as to be movable in the longitudinal axis direction.

The drive mechanism 5 slides the holder 6 along the longitudinal axis direction inside the housing body 10 of the first grasper 3, and is connected to the proximal end surface of the holder 6. When a pushing force is applied to the drive mechanism 5 in the longitudinal axis direction, the holder 6 inside the housing body 10 of the first grasper 3 moves between a first position P1 (see FIG. 6A) at which the fixing pin 18 in the first slits 19a is at the distal end side to a third position P3 (see FIG. 6D) at which the fixing pin 18 in the second slits 19b is at the proximal end side via a second position P2 (see FIG. 6B) at which the fixing pin 18 in the first slits 19a is at the proximal end side. The holder 6 is fixed to the first grasper 3 with the fixing pins 18 passed through the first slits 19a and the second slits 19b; thus, as illustrated in FIGS. 3A and 3B, the movement of the holder 6 in the longitudinal axis direction is limited to the range in which the fixing pins 18 can move, which is between the distal end portion of the first slits 19a and the proximal end portion of the second slits 19b.

As illustrated in FIGS. 2 and 3B, when the first grasper 3 and the second grasper 4 are in a closed state and the holder 6 is placed at the first position P1 on the distal-most side of the first grasper 3 by using the drive mechanism 5, the needle tip 7d of the second needle 7b of the staple 7 penetrating through the tissue A is inside the recessed portion 11 in the second grasper 4. Thus, even in a closed state, the needle tip 7d of the staple 7 remains unexposed.

Figure 6A:
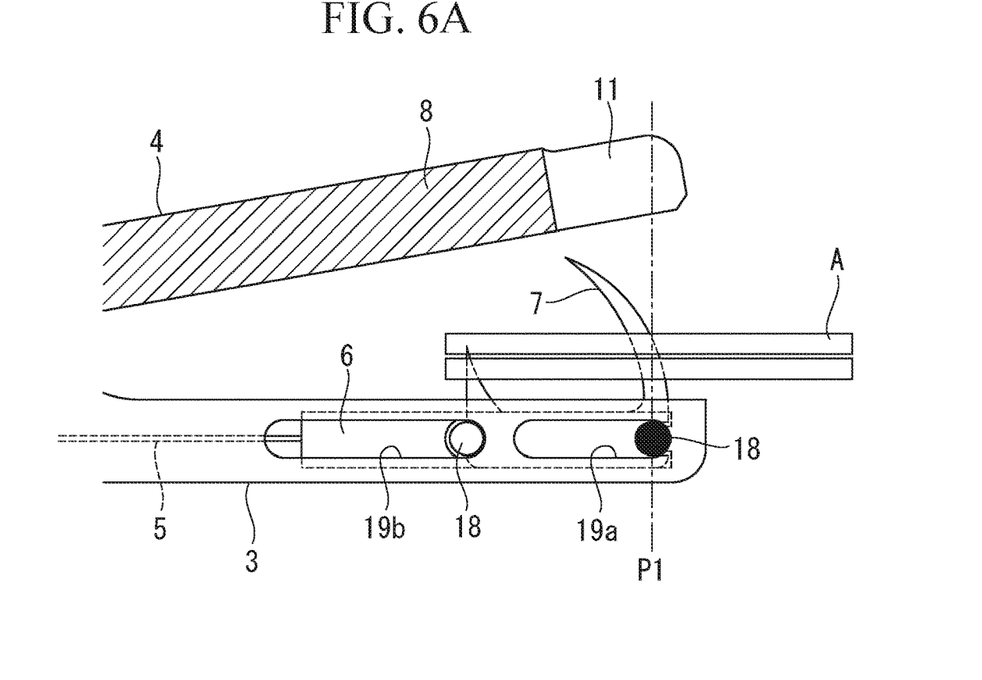
FIG. 6A is a vertical sectional view illustrating a state in which tissue is punctured by a staple in the medical stapler system illustrated in FIG. 1.
Figure 6B:
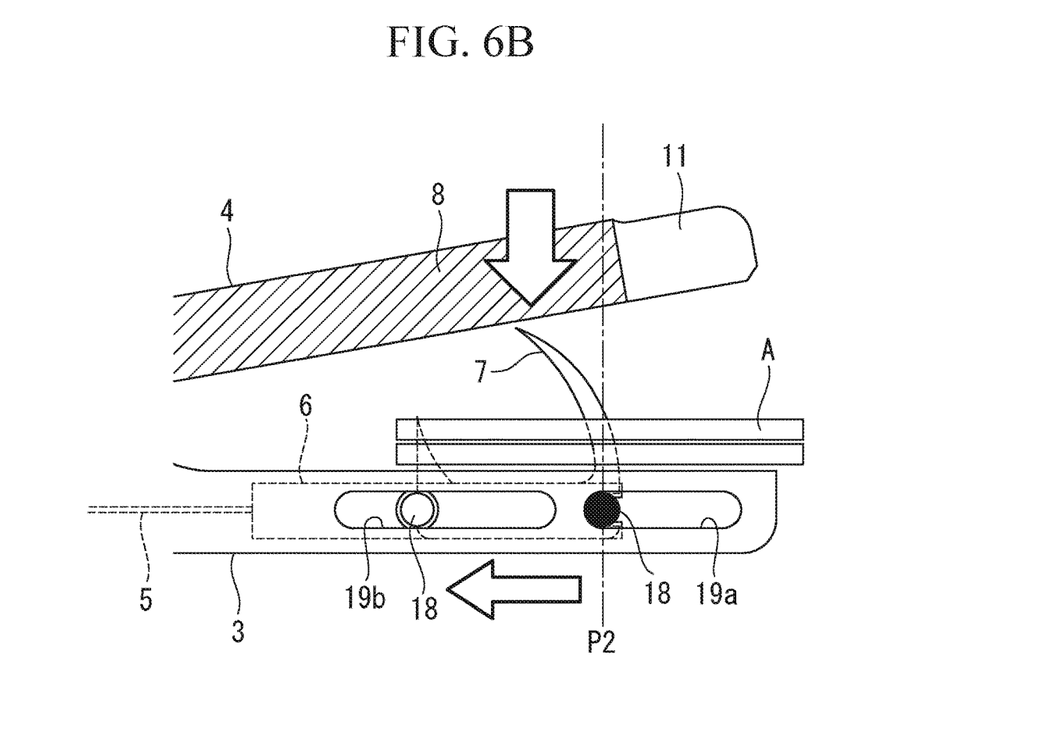
FIG. 6B is a vertical sectional view illustrating transition from the state illustrated in FIG. 6A to a state in which the medical stapler grasping the tissue is closed.

As illustrated in FIG. 6B, when the first grasper 3 and the second grasper 4 are in an open state and the holder 6 is placed at the second position P2 by using the drive mechanism 5, the needle tip 7d of the second needle 7b of the staple 7 is at a position corresponding to the anvil 8 of the second grasper 4. In this state, when the first grasper 3 and the second grasper 4 are switched to a closed state, the needle tip 7d of the second needle 7b hits the anvil 8 of the second grasper 4 and receives an external force in a direction in which the needle tip 7d bends further (see FIG. 6C).

Figure 6C:
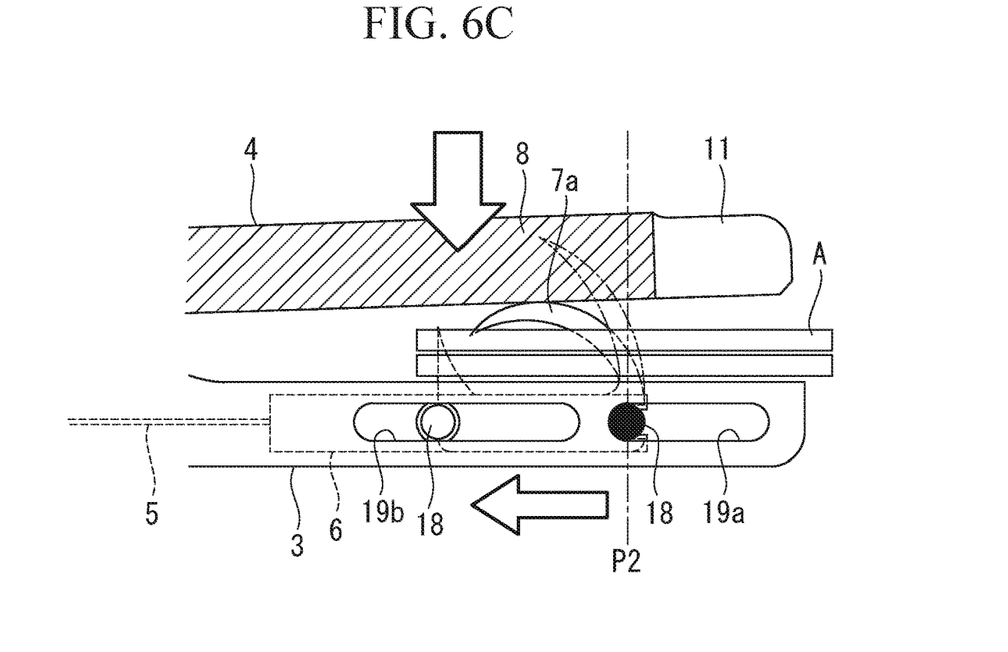
FIG. 6C is a vertical sectional view illustrating a state in which a needle of the staple is bent from the state illustrated in FIG. 6B.
Figure 6D:
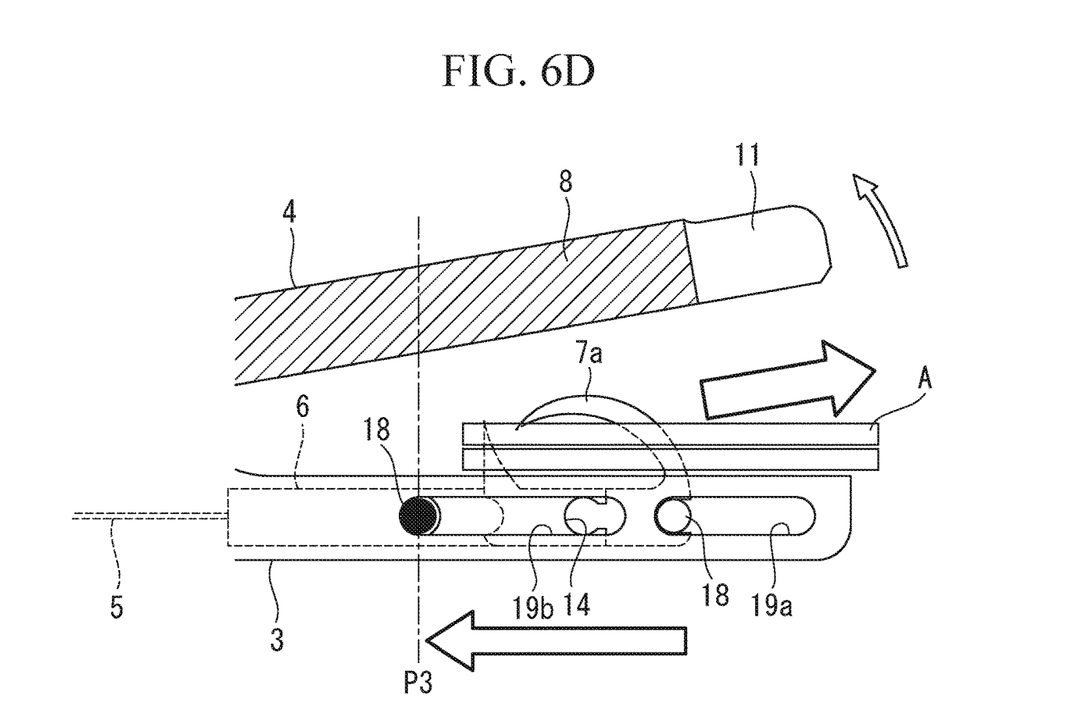
FIG. 6D is a vertical sectional view illustrating a state in which a second needle of the staple is again made to penetrate through the tissue from the state illustrated in FIG. 6C so as to complete closure.

As illustrated in FIG. 6D, as the external force from the anvil 8 of the second grasper 4 is further applied, the needle tip 7d of the second needle 7b is extensively bent and becomes folded, puncturing the tissue A again. As such, the tissue A can be appropriately closed as the second needle 7b of the staple 7 is bent to wrap around the tissue A.

Subsequently, while the first grasper 3 and the second grasper 4 are maintained in the closed state, the holder 6 is further moved to the third position P3 on the proximal end side so that the fixing pin 18 detaches from the fitting recessed portion 14 and the staple 7 is released from the holder 6.

The effects of the medical stapler system 1 of this embodiment configured as described above will now be described.

In order to close the tissue A by using the medical stapler system 1 of this embodiment, first, the holder 6 is placed at the first position P1 so as to create a closed state (see FIG. 3B) in which the staple 7 is housed in the recessed portion 11, and is introduced up to a position near an affected site. Next, the pivot mechanism 9 is driven to cause the second grasper 4 to pivot on the pivot axis with respect to the first grasper 3 so as to create an open state in which the first grasper 3 and the second grasper 4 are separated from each other (see FIG. 3A).

Subsequently, the tissue A to be closed is placed between the first contact surface 3a of the first grasper 3 and the second contact surface 4a of the second grasper 4, and the pivot mechanism 9 is actuated to put the first grasper 3 and the second grasper 4 in a closed state. Since the staple 7 is on the distal end side of the first grasper 3, the needle tips of the first needle 7a and the second needle 7b of the staple 7 cut into and penetrate through the tissue A grasped between the first contact surface 3a of the first grasper 3 and the second contact surface 4a of the second grasper 4 present on both right and left sides of the recessed portion 11. Then, as illustrated in FIG. 6A, the pivot mechanism 9 is actuated again to put the first grasper 3 and the second grasper 4 in an open state.

In this state, a driving force that moves the holder 6 retaining the staple 7 toward the proximal end side of the first grasper 3 is applied to the drive mechanism 5 so as to move the holder 6 along the first slits 19a and the second slits 19b in the first grasper 3 up to the second position P2 at which the fixing pin 18 in the first slits 19a is positioned on the proximal end side (see FIG. 6B).

Next, the pivot mechanism 9 is actuated to put the second grasper 4 and the first grasper 3 in a closed state; as a result, as illustrated in FIG. 6C, the needle tip 7d of the second needle 7b of the staple 7 hits the anvil 8 and receives an external force, and thus the needle tip 7d of the second needle 7b is bent and folded toward the tissue A and punctures the tissue A again. Thus, the tissue A can be securely closed by the staple 7.

Furthermore, from this state, as illustrated in FIG. 6D, while the first grasper 3 and the second grasper 4 are maintained in a closed state, the holder 6 is further moved up to the third position P3 on the proximal end side. This causes the fixing pin 18 in the first slits 19a to stop at a position in the proximal end portion of the first slits 19a and to detach from the fitting recessed portion 14 in the distal end side end portion of the holder 6, during which the fixing pin 18 also detaches from the pin receiving portions 13 on the distal end side of the staple 7. During this process, since the holder 6 moves until reaching a position where the fixing pin disposed in the second slits 19b reaches a position in the proximal end portion of the second slits 19b while leaving the staple 7 in the middle, the fixing pin 18 also detaches from the pin receiving portions 13 on the proximal end side of the staple 7, and the staple 7 is released from the holder 6.

Next, the pivot mechanism 9 is driven to put the first grasper 3 and the second grasper 4 in an open state again. The released staple 7 is discharged to outside together with the closed tissue A.

As such, according to the medical stapler system 1 of this embodiment, during the introduction of the medical stapler 2 into the body, the needle tip 7d of the staple 7 remains unexposed even when the first grasper 3 and the second grasper 4 are in a closed state; thus, the medical stapler 2 can be safely introduced to the site to be treated. In addition, while the medical stapler 2 is placed inside the body, the tissue A can be closed with the staple 7 by combining closing and opening of the first grasper 3 and the second grasper 4 and the movement of the staple 7 in the longitudinal axis direction. Thus, there is no need to separately secure a space in the medical stapler 2 to protect the needle tip 7d of the staple 7 from the outside, and there is an advantage in that the diameter of the medical stapler system 1 can be reduced.

During the puncturing, the second contact surface 4a of the second grasper 4 present on both sides of the recessed portion 11 presses the tissue A against the first contact surface 3a of the first grasper 3 so that the tissue A does not slip away, and closure can be performed with stability. Since the second needle 7b of the staple 7 has a curved shape, when the staple 7 is bent by a pressing force from the anvil 8, the needle tip 7d of the second needle 7b bends and become folded toward the tissue A, and thus, the tissue A can be appropriately closed.

The staple 7 closing the tissue A can be easily released and discharged by merely moving the holder 6 housed in the first grasper 3 in the longitudinal axis direction.

Since the holder 6 is equipped with an attach-release mechanism 20 that retains the staple 7 at the first position P1 where the second needle 7b of the staple 7 is housed in the recessed portion 11 and that releases the staple 7 at the third position P3 where the second needle 7b of the staple 7 is deformed by the anvil 8, the staple 7 that has appropriately closed the tissue A can be easily detached and discharged from the medical stapler 2 by merely retaining the staple at the first position P1 and releasing the staple 7 at the third position P3.

Figure 7:
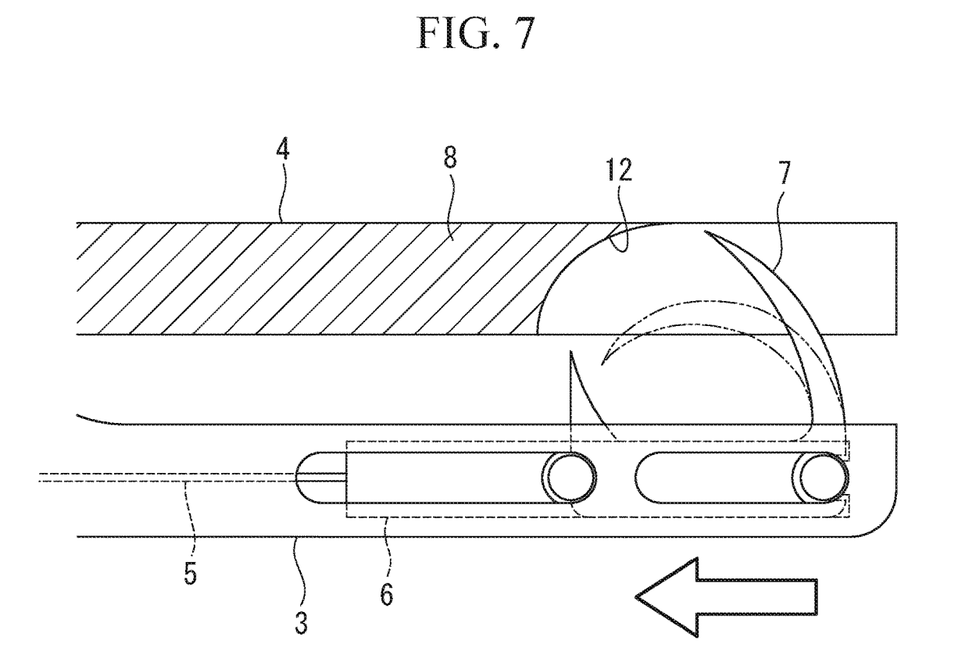
FIG. 7 is a horizontal sectional view illustrating a modification of a medical stapler used in the medical stapler system illustrated in FIG. 1, and illustrates a state in which a curved surface is formed in an anvil.

In this embodiment, as illustrated in FIG. 7, the anvil 8 of the second grasper 4 may have a curved surface 12 that is adjacent to the recessed portion 11 in the longitudinal axis direction and that guides and bends the second needle 7b as the holder 6 is made to slide in the closed state.

In this manner, the second needle 7b of the staple 7 can be bent along the curved surface and the tissue A can be closed by merely moving the holder 6 retaining the staple 7 from the distal end side to the proximal end side by driving the drive mechanism 5 while maintaining the first grasper 3 and the second grasper 4 in a closed state.

Figure 5B:
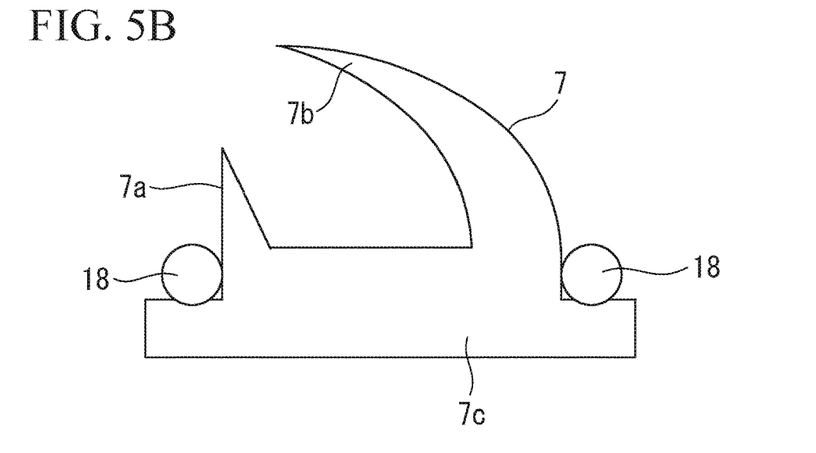
FIG. 5B is a vertical sectional view illustrating a first modification of the staple illustrated in FIG. 5A.

In this embodiment, an example in which the pin receiving portions 13 that detachably receive the fixing pins 18 are provided on both ends of the base portion 7c of the staple 7 is described; alternatively, as illustrated in FIG. 5B, the pin receiving portions 13 may be a space defined by the upper surface of the base portion 7c and the outer surface of the first needle 7a and a space defined by the upper surface of the base portion 7c and the outer surface of the second needle 7b.

Figure 5C:
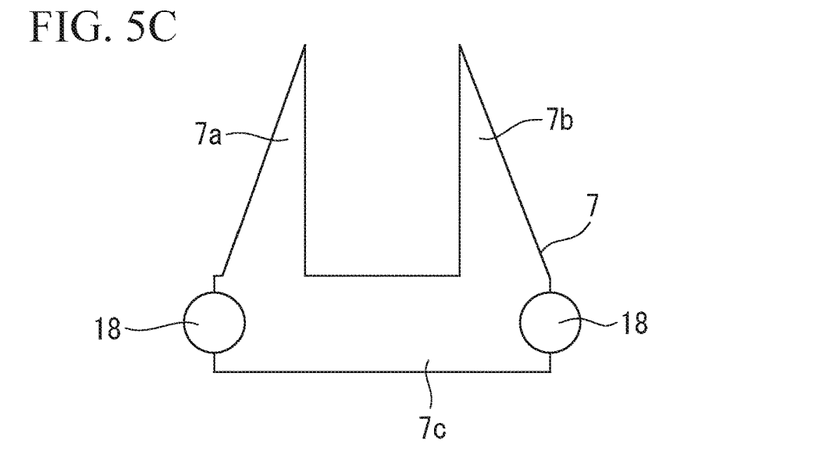
FIG. 5C is a vertical sectional view illustrating a second modification of the staple illustrated in FIG. 5A.

In this embodiment, a staple 7 having a curved form is employed so that the second needle 7b can be easily bent; alternatively, as illustrated in FIG. 5C, a symmetric staple 7 having a straight second needle 7b in a mirror image relationship with the first needle 7a may be employed.

Figure 8:
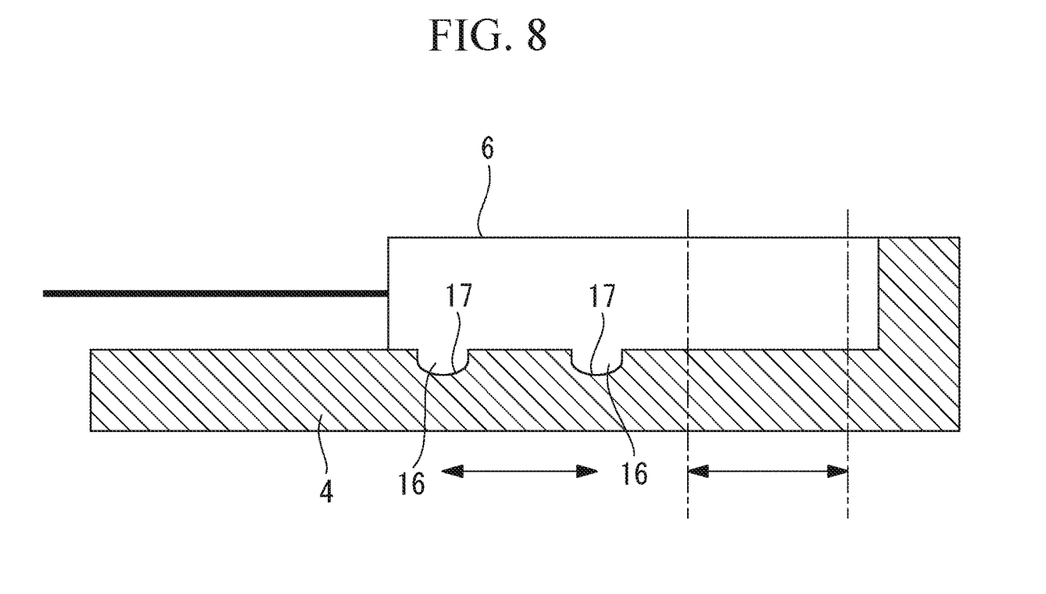
FIG. 8 is a horizontal sectional view illustrating a modification of the medical stapler system illustrated in FIG. 1.

In this embodiment, an example in which the movement range of the holder 6 in the longitudinal axis direction is limited by the fixing pins 18 inserted into the first slits 19a and the second slits 19b in the first grasper 3 is described; alternatively, as illustrated in FIG. 8, projections 16 may be formed at the bottom of the holder 6, and grooves 17 that fit with the projections 16 may be formed in the inner surface of the first grasper 3 so as to set the position of the holder 6 and limit the movement range of the holder 6.

The fixing pins 18 may be formed of a plastic or the like that can deform under an external force, or an elastic material, such as a spring, may be connected to the fixing pins 18 so as to retain the staple 7 in the holder 6. In this manner, the staple 7 that has closed the tissue A can be more easily discharged.

Projections or the like that inhibit detachment of the staple 7 may be formed on the side surfaces of the groove in the holder 6 in which the base portion 7c of the staple 7 is fitted.

It should be noted that, in this embodiment, an example in which one staple 7 is placed in a direction along the longitudinal axis direction is described to simplify illustration and description; however, the number of staples 7 and the number of rows of staples 7 can be any.

As a result, the following aspects are derived from the above-described embodiments.

According to an aspect of the present invention, there is provided a medical stapler system including a medical stapler and a staple to be deformed by the medical stapler to close tissue. The medical stapler includes: a first grasper and a second grasper that are pivotably connected to each other so as to be openable and closable relative to each other and that have a longitudinal axis so that the tissue can be grasped between the first and second graspers when in a closed state; a holder that retains the staple; a housing body that houses the holder while needles of the staple project from a first contact surface of the first grasper to be closely attached to the tissue when in the closed state; and a drive mechanism that slides the holder in the housing body along the longitudinal axis. The second grasper has a second contact surface that graspes the tissue between the first contact surface and the second contact surface when in the closed state. The second contact surface has a recessed portion that can house the needles without causing penetration or deformation when the closed state is created and the holder is positioned on one side in the longitudinal axis direction, and an anvil against which the needles are pushed and deformed when the closed state is created and the holder is positioned on the other side in the longitudinal axis direction.

According to this aspect, when the holder retaining the staple is placed on one side in the longitudinal axis direction and the first grasper and the second grasper of the medical stapler are put in a closed state, the needles of the staple are housed in the recessed portion of the second grasper. Thus, during introduction of the medical stapler into the body, the needle tips of the staple remain unexposed even when the first grasper and the second grasper are in a closed state, and the medical stapler can be safely introduced to the site to be treated. In addition, while the medical stapler is placed inside the body, the tissue can be closed with the staple by combining closing and opening of the first grasper and the second grasper and the movement of the staple in the longitudinal axis direction.

Meanwhile, when the holder is made to slide to the other side in the longitudinal axis direction by actuating the drive mechanism, the needle of the staple comes at a position facing the anvil of the second grasper. Thus, by bringing the first grasper and the second grasper into a closed state, the needle can be pressed and deformed against the anvil, and the tissue can be closed.

As a result, there is no need to separately secure a space in the medical stapler to protect the needle tip from outside, the diameter of the medical stapler can be reduced, and the medical stapler can be easily delivered to a site to be treated by using the medical stapler system through an access port with a limited inner diameter, such as an endoscope channel or a surgical trocar.

In the aspect described above, the staple may have an elongated base portion, the needles may include a first needle having a sharp-pointed shape extending from one end of the base portion in a direction orthogonal to a lengthways direction of the base portion, and a second needle 7b extending from the other end of the base portion in the direction orthogonal to the lengthways direction of the base portion, the second needle having a needle tip having a curved shape smoothly bending toward the first needle. The staple may be placed so that the base portion extends along the longitudinal axis direction of the medical stapler 2.

In this manner, since the base portion of the staple extends along the longitudinal axis direction of the medical stapler, the diameter of the medical stapler can be reduced compared to when the base portion of the staple extends in a direction orthogonal to the longitudinal axis direction of the medical stapler. Thus, the diameter of the medical stapler system can be reduced.

In addition, since the second needle of the staple has a smoothly bending curved shape, pressing the second needle with the anvil further bends the needle tip of the second needle as if the needle tip is collapsed toward the first needle side, and the second needle punctures and wraps the tissue. As a result, the tissue can be securely closed with the staple.

In the aspect described above, the anvil may have a curved surface that is adjacent to the recessed portion in the longitudinal axis direction and that guides and bends the second needle as the holder is made to slide in the closed state.

In this manner, the second needle of the staple can be bent along the curved surface of the anvil and the tissue can be closed by merely sliding the holder retaining the staple toward the proximal end side while maintaining the first grasper and the second grasper of the medical stapler in the closed state.

In the aspect described above, the holder may be equipped with an attach-release mechanism that retains the staple at a position where the needles of the staple are housed in the recessed portion and releases the staple at a position where the needles of the staple are deformed by the anvil.

In this manner, the staple that has appropriately closed the tissue can be easily detached and discharged from the medical stapler by using the attach-release mechanism, with which the holder retains the staple at a position where the needles of the staple are housed in the recessed portion and releases the staple at a position where the needles of the staple are deformed by the anvil.

REFERENCE SIGNS LIST 1 medical stapler system
2 medical stapler
3 first grasper
4 second grasper
5 drive mechanism
6 holder
7 staple
7a first needle (needle)
7b second needle (needle)
7c base portion
8 anvil
10 housing body
11 recessed portion
12 curve surface
13 pin receiving portion
18 fixing pin
19a first slit
19b second slit
20 attach-release mechanism
A tissue
P1 first position
P2 second position
P3 third position

The invention claimed is:
1. A medical stapler system comprising:
a medical stapler; and
a staple that is configured to be deformed by the medical stapler to close tissue, wherein:

the medical stapler includes:

a first grasper and a second grasper that are pivotably connected to each other so as to open and close relative to each other and that have a longitudinal axis so that the tissue is grasped between the first and second graspers when in a closed state;

a holder that retains the staple;

a housing body that houses the holder while needles of the staple project from a first contact surface of the first grasper to be closely attached to the tissue when in the closed state; and a drive mechanism that is configured to slide the holder in the housing body along the longitudinal axis, wherein the second grasper has a second contact surface that grasps the tissue between the first contact surface and the second contact surface when in the closed state, and a recessed portion that is formed on the second contact surface and that houses the needles without causing penetration or deformation when the closed state is created and the holder is positioned on one side in the longitudinal axis direction, and an anvil against which the needles are pushed and deformed when the closed state is created and the holder is positioned on the other side in the longitudinal axis direction.

2. The medical stapler system according to claim 1, wherein:

the staple has an elongated base portion, the needles include
- a first needle having a sharp-pointed shape extending from one end of the base portion in a direction orthogonal to a lengthways direction of the base portion, and
- a second needle extending from the other end of the base portion in the direction orthogonal to the lengthways direction of the base portion, the second needle having a needle tip having a curved shape smoothly bending toward the first needle, wherein the staple is placed so that the base portion extends along the longitudinal axis direction of the medical stapler.

3. The medical stapler system according to claim 2, wherein the anvil has a curved surface that is adjacent to the recessed portion in the longitudinal axis direction and that guides and bends the second needle as the holder is made to slide in the closed state.

4. The medical stapler system according to claim 1, wherein the holder is equipped with an attach-release mechanism that is configured to retain the staple at a position where the needles of the staple are housed in the recessed portion and to release the staple at a position where the needles of the staple are deformed by the anvil.

* * * * *